(12) United States Patent
Funke et al.

(10) Patent No.: US 10,189,799 B2
(45) Date of Patent: Jan. 29, 2019

(54) PROCESS FOR PREPARING SUBSTITUTED PHENYLISOXAZOLINE DERIVATIVES

(71) Applicant: BAYER CROPSCIENCE AKTIENGESELLSCHSAFT, Monheim am Rhein (DE)

(72) Inventors: Christian Funke, Leichlingen (DE); Jens Dietmar Heinrich, Leverkusen (DE); Sergii Pazenok, Solingen (DE); Norbert Lui, Odenthal (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/548,216

(22) PCT Filed: Feb. 29, 2016

(86) PCT No.: PCT/EP2016/054192
§ 371 (c)(1),
(2) Date: Aug. 2, 2017

(87) PCT Pub. No.: WO2016/139164
PCT Pub. Date: Sep. 9, 2016

(65) Prior Publication Data
US 2018/0030002 A1   Feb. 1, 2018

(30) Foreign Application Priority Data
Mar. 5, 2015  (EP) .................................. 15157803

(51) Int. Cl.
*C07D 261/04* (2006.01)
*C07D 261/08* (2006.01)
(52) U.S. Cl.
CPC ......... *C07D 261/04* (2013.01); *C07D 261/08* (2013.01)

(58) Field of Classification Search
None
See application file for complete search history.

(56) References Cited

U.S. PATENT DOCUMENTS

| | | | |
|---|---|---|---|
| 6,645,919 B1 | 11/2003 | Baumann et al. | |
| 9,375,009 B2 * | 6/2016 | Tsuchiya | C07D 419/14 |
| 9,717,243 B2 | 8/2017 | Hillebrand et al. | |

FOREIGN PATENT DOCUMENTS

| | | |
|---|---|---|
| WO | 0187856 A1 | 11/2001 |
| WO | 2008/013925 A2 | 1/2008 |
| WO | 2009/094407 A2 | 7/2009 |
| WO | 2010/123791 A1 | 10/2010 |
| WO | 2011/072207 A1 | 6/2011 |
| WO | 2011/085170 A1 | 7/2011 |
| WO | 2013/098229 A2 | 7/2013 |
| WO | 2014/206896 A1 | 12/2014 |

OTHER PUBLICATIONS

Kenichi Murai et al: "Reactivity of the ester group attached isoxazoline, benzisoxazole, and isoxazole: a facial preparation of 3-acyl-substituted these heterocycles", Tetrahedron Letters, Pergamon, vol. 53, May 2, 2012, p. 3746-3749.
Kenichi Murai et al: "Supporting Information" Graduate School of Pharmaceutical Sciences. May 7, 2012 , p. S1-S62. XP055187341.
Alan P. Kozikowski et al: "Methods for the Stereoselective Cis Cyanhydroxylation and Carboxyhydroxylation of Olefins", The Journal of Organic Chem., vol. 48, Feb. 1, 1983, p. 366-372.

* cited by examiner

*Primary Examiner* — Kamal A Saeed
(74) *Attorney, Agent, or Firm* — McBee Moore Woodward & Vanik IP, LLC

(57) ABSTRACT

The present invention relates to a process for preparing substituted phenylisoxazoline derivatives.

4 Claims, No Drawings

PROCESS FOR PREPARING SUBSTITUTED PHENYLISOXAZOLINE DERIVATIVES

CROSS REFERENCE TO RELATED APPLICATIONS

This application is a § 371 National State Application of PCT/EP2016/054192, filed Feb. 2, 2016, which claims priority to European Application No. 15157803.6 filed Mar. 5, 2015.

BACKGROUND

Field of the Invention

The present invention relates to a process for preparing substituted phenylisoxazoline derivatives.

Description of Related Art

Substituted phenylisoxazoline derivatives are useful intermediates in the production of active agrochemical ingredients (see, for example, WO 2008/013925, WO 2009/094407, WO 2010/123791).

There are various known processes for preparing such substituted phenylisoxazoline derivatives.

WO 2011/085170 describes, for example, a process for preparing these phenylisoxazoline derivatives by [3+2] cycloaddition with a chloroxime with a styrene and downstream Grignard addition and halogenation (Scheme 1).

Scheme 1:

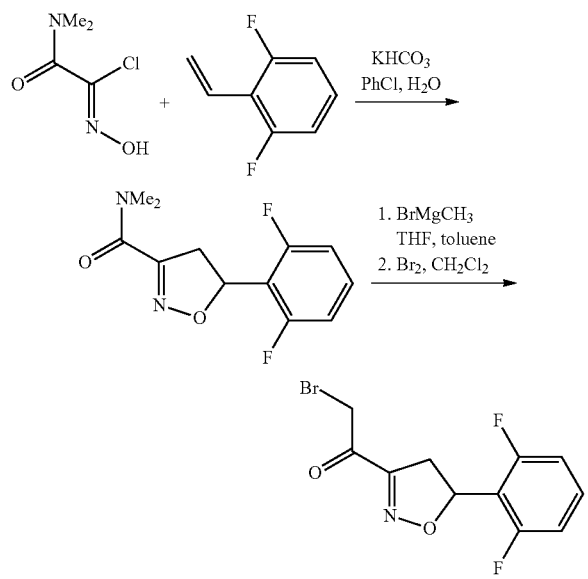

A disadvantage of this process is that the use of further functional groups which can react directly with a Grignard reagent is impossible.

WO 2011/085170 describes, for example, a process for preparing these phenylisoxazoline derivatives by [3+2] cycloaddition with a chloroxime with a styrene and downstream halogenation (Scheme 2).

Scheme 2:

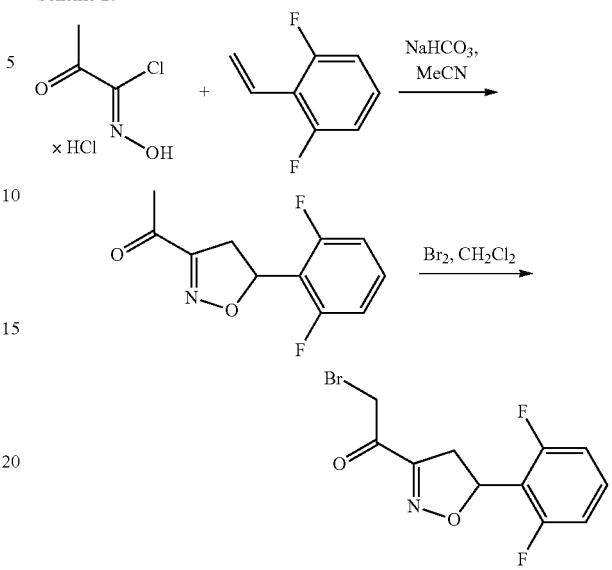

Disadvantages of this process are the technically complex preparation of the chloroxime shown.

WO 2011/072207 describes a [3+2] cycloaddition proceeding from a styrene with a chloroxime containing the required haloketone (Scheme 3).

Scheme 3:

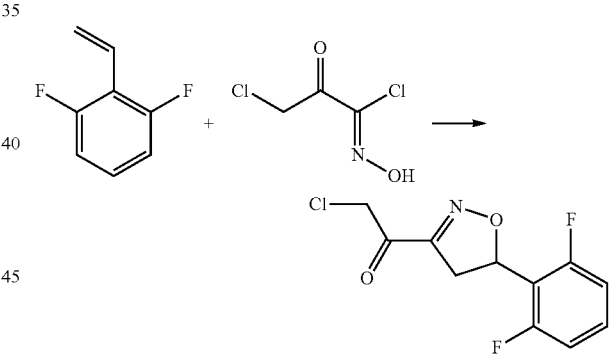

Disadvantages of this process are the technically difficult preparation of the chloroxime shown and the large excesses required.

WO 2008/013925 describes the reaction of dichloroacetone with tert-butyl nitrite and the subsequent [3+2] cycloaddition with a styrene (Scheme 4).

Scheme 4:

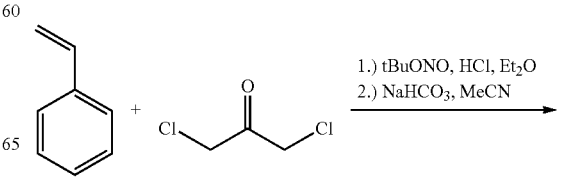

-continued

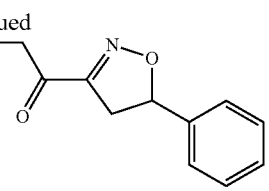

A disadvantage of this process is that dichloroacetone is not available in industrial volumes and the reaction with tert-butyl nitrite is demanding for safety reasons.

Because of the importance of substituted phenylisoxazoline derivatives as a unit for synthesis of novel active agrochemical ingredients, the problem addressed is that of finding a process which can be used on the industrial scale and inexpensively. It is also desirable to obtain the specific phenylisoxazoline derivatives with high yield and high purity, such that the target compound preferably does not have to be subjected to any further potentially complex purification.

SUMMARY

This problem was solved by a process for preparing substituted phenylisoxazoline derivatives of the formula (I):

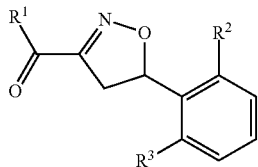

(I)

in which
$R^1$ is methyl, bromomethyl or chloromethyl;
$R^2$ is halogen, $C_1$-$C_4$-alkyl, $C_1$-$C_4$-alkoxy, $C_1$-$C_4$-haloalkyl and
$R^3$ is $C_1$-$C_4$-alkylsulphonyloxy, $C_1$-$C_4$-haloalkylsulphonyloxy,
characterized in that, in step (i), a chloroxime of the formula (II)

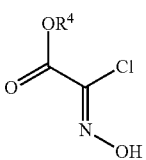

(II)

in which $R^4$ is $C_1$-$C_{12}$-alkyl,
is reacted with a styrene of the formula (III)

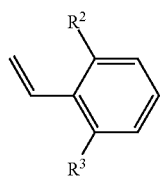

(III)

in which $R^2$ and $R^3$ are as defined above,
in the presence of an inorganic base in an organic aprotic solvent to give the corresponding phenylisoxazoline of the formula (IV)

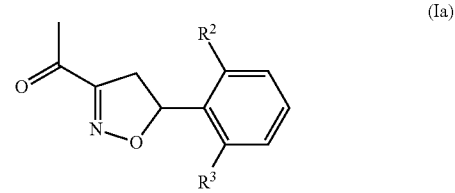

(IV)

in which $R^2$, $R^3$ and $R^4$ are as defined above,
and the latter then reacts, in step (ii), with an organometallic reagent and an organic base in an organic aprotic solvent to give the ketone of the formula (Ia)

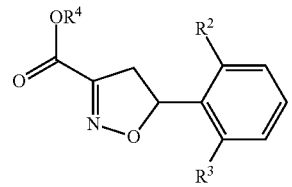

(Ia)

in which $R^2$ and $R^3$ are as defined above,
and then, in step (iii), in the presence of a halogenating agent in a solvent, the haloketone of the formula (Ib) is formed

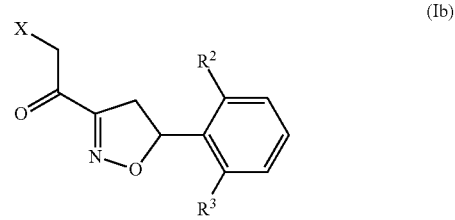

(Ib)

in which $R^2$ and $R^3$ are as defined above and
X is chlorine or bromine.

DETAILED DESCRIPTION OF A PREFERRED EMBODIMENT

Preference is given to a process according to the invention in which the radical definitions of the formulae (I), (Ia), (Ib), (II), (III) and (IV) are as follows:
$R^1$ is methyl, bromomethyl, chloromethyl;
$R^2$ is chlorine or bromine;
$R^3$ is methylsulphonyloxy or ethylsulphonyloxy;
$R^4$ is $C_1$-$C_4$-alkyl and
X is chlorine or bromine.
Particular preference is given to a process according to the invention in which the radical definitions of the formulae (I), (Ia), (Ib), (II), (III) and (IV) are as follows:
$R^1$ is methyl, bromomethyl;
$R^2$ is chlorine;
$R^3$ is methylsulphonyloxy;
$R^4$ is methyl, ethyl and
X is bromine.

A further aspect of the present invention is compounds of the formula (IV):

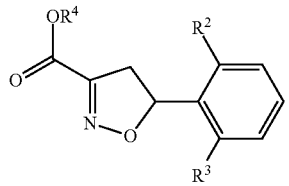

(IV)

in which
R² is halogen, $C_1$-$C_4$-alkyl, $C_1$-$C_4$-alkoxy, $C_1$-$C_4$-haloalkyl;
R³ is $C_1$-$C_4$-alkylsulphonyloxy, $C_1$-$C_4$-haloalkylsulphonyloxy and
R⁴ is $C_1$-$C_{12}$-alkyl.

Preference is given to compounds of the formula (IV) in which
R² is chlorine or bromine;
R³ is methylsulphonyloxy or ethylsulphonyloxy and
R⁴ is $C_1$-$C_4$-alkyl.

Particular preference is given to compounds of the formula (IV)
in which
R² is chlorine;
R³ is methylsulphonyloxy and
R⁴ is methyl, ethyl.

A further aspect of the present invention is compounds of the formula (Ia):

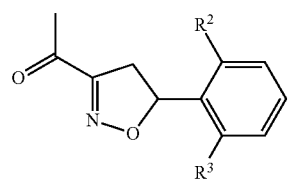

(Ia)

in which
R² is halogen, $C_1$-$C_4$-alkyl, $C_1$-$C_4$-alkoxy, $C_1$-$C_4$-haloalkyl and
R³ is $C_1$-$C_4$-alkylsulphonyloxy, $C_1$-$C_4$-haloalkylsulphonyloxy.

Preference is given to compounds of the formula (Ia) in which
R² is chlorine or bromine and
R³ is methylsulphonyloxy or ethylsulphonyloxy.

Particular preference is given to compounds of the formula (Ia)
in which
R² is chlorine and
R³ is methylsulphonyloxy.

A further aspect of the present invention is compounds of the formula (Ib):

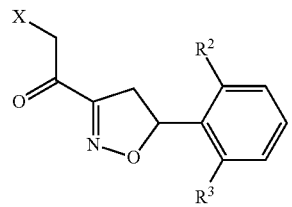

(Ib)

in which
R² is halogen, $C_1$-$C_4$-alkyl, $C_1$-$C_4$-alkoxy, $C_1$-$C_4$-haloalkyl;
R³ is $C_1$-$C_4$-alkylsulphonyloxy, $C_1$-$C_4$-haloalkylsulphonyloxy and
X is chlorine or bromine.

Preference is given to compounds of the formula (Ib) in which
R² is chlorine or bromine;
R³ is methylsulphonyloxy or ethylsulphonyloxy and
X is chlorine or bromine.

Particular preference is given to compounds of the formula (Ib)
in which
R² is chlorine;
R³ is methylsulphonyloxy and
X is bromine.

General Definitions

In the definitions of the symbols given in the above formulae, collective terms which are generally representative of the following substituents were used:

Halogen: fluorine, chlorine, bromine and iodine;

Alkyl: saturated straight-chain or branched hydrocarbyl radicals having 1 to 12 carbon atoms, for example (but not limited to) $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Alkylsulphonyl: saturated, straight-chain or branched alkylsulphonyl radicals having 1 to 4 carbon atoms, for example (but not limited to) $C_1$-$C_6$-alkylsulphonyl such as methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl;

Haloalkyl: straight-chain or branched alkyl groups having 1 to 4 carbon atoms (as specified above), where some or all of the hydrogen atoms in these groups may be replaced by halogen atoms as specified above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl;

Alkoxy: saturated straight-chain or branched alkoxy radicals having 1 to 4 carbon atoms, for example (but not limited to) methoxy, ethoxy, propoxy, 1-methylethoxy, butoxy, 1-methylpropoxy, 2-methylpropoxy, 1,1-dimethylethoxy. This definition also applies to alkoxy as part of a composite substituent, for example haloalkoxy, alkynylalkoxy etc., unless defined elsewhere.

Description of the Process

The reaction according to the invention is shown in Scheme 5.

Scheme 5:

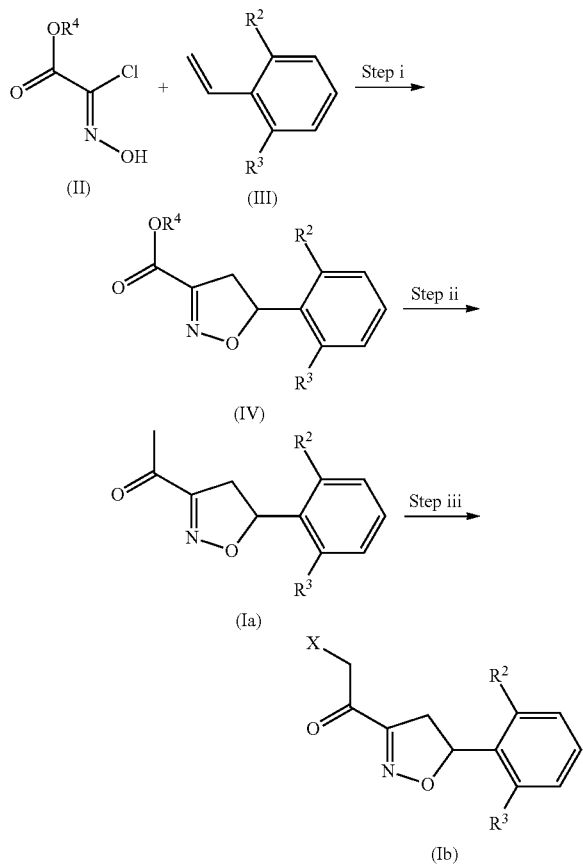

The desired phenylisoxazoline derivatives of the general formula (I) are obtained with good yields and in high purity by the process according to the invention.

The process according to the invention has the advantage over the processes described above that the starting materials are preparable on the industrial scale and the process is surprisingly compatible with base-labile alkylsulphonyloxy and haloalkylsulphonyloxy groups.

The application accordingly relates to a process for preparing particular phenylisoxazoline derivatives of the general formula (II), comprising the following steps:

Step (i):

Reacting the chloroxime of the formula (II) with a styrene of the formula (III) in the presence of an organic base and an organic aprotic solvent to give the corresponding isoxazoline of the formula (IV).

Useful solvents for the process according to the invention are in principle any organic aprotic solvents or solvent mixtures that are inert under the reaction conditions, including ketones, for example acetone, diethyl ketone, methyl ethyl ketone and methyl isobutyl ketone; nitriles, for example acetonitrile and butyronitrile; ethers, for example dimethoxyethane (DME), tetrahydrofuran (THF), 2-methyl-THF and 1,4-dioxane; hydrocarbons and halogenated hydrocarbons such as hexane, heptane, cyclohexane, methylcyclohexane, toluene, ortho-xylene, meta-xylene, para-xylene, mesitylene, chlorobenzene, ortho-dichlorobenzene or nitrobenzene; esters, for example methyl acetate, ethyl acetate, n-propyl acetate, isopropyl acetate, n-butyl acetate, isobutyl acetate, sec-butyl acetate, hexyl acetate, cyclohexyl acetate, 2-ethylhexyl acetate. Preferably, the solvent is selected from the group of the esters: methyl acetate, ethyl acetate, n-propyl acetate, isopropyl acetate, n-butyl acetate, isobutyl acetate, sec-butyl acetate, hexyl acetate, cyclohexyl acetate, 2-ethylhexyl acetate or mixtures of these solvents or of the nitriles: acetonitrile, butyronitrile. More preferably, ethyl acetate and isobutyl acetate are used.

Suitable inorganic bases include carbonates (for example lithium carbonate, sodium carbonate, sodium hydrogencarbonate, potassium carbonate and calcium carbonate), phosphates (for example potassium phosphate, sodium phosphate and lithium phosphate) and hydroxides (for example potassium hydroxide, sodium hydroxide and lithium hydroxide). Preferably, $Na_2CO_3$ and $NaHCO_3$ are used.

The temperature in the process according to the invention can be varied within wide limits. A customary operating temperature is from $-10°$ C. to $60°$ C., preferably from $5°$ C. to $50°$ C. More preferably, the reaction is conducted at a temperature in the range from $10°$ C. to $40°$ C.

The process according to the invention is typically conducted at standard pressure. It is also possible to conduct the reaction under reduced pressure or under elevated pressure.

The molar ratios of the compound of the formula (II) to the compound of the formula (III) and to the inorganic base may vary within wide ranges. They are generally not subject to any restriction.

In step (i), it is advantageous when the molar ratio of the compound of the formula (II) to the compound of the formula (III) is in the range from 0.9 to 3.0, preferably in the range from 1.0 to 2.0. More preferably, the molar ratio is in the range from about 1.0 to 1.5. It is preferable that the molar ratio of the compound of the formula (II) to the inorganic base is in the range from 0.1 to 1.0, more preferably in the range from 0.2 to 1.0. More preferably, the molar ratio is in the range from 0.25 to 1.0.

The chloroximes of the formula (II) are known from the literature and some are available in industrial volumes (see, for example, *Tetrahedron Letters* 2011, Volume 52, Issue 43, 5656-5658).

The styrenes of the formula (III) can be prepared by general synthesis methods; see, for example, Organic Synthesis 1928, 8, 84; Organic Synthesis 1948, 28, 31; Organic Synthesis 1953, 33, 62; Organic Synthesis 1966, 46, 89; Organic Synthesis 2006, 83, 45.

The reaction time is short and is in the range from 0.5 to 5 hours. A longer reaction time is possible, but is not economically worthwhile.

Step (ii):

Reacting the phenylisoxazoline of the formula (IV) with an organometallic reagent and an organic base in an organic aprotic solvent to give the ketone of the formula (Ia).

Useful solvents for the process according to the invention in principle include any organic aprotic solvents or solvent mixtures that are inert under the reaction conditions, including: ethers, for example dimethoxyethane (DME), tetrahydrofuran (THF), 2-methyl-THF and 1,4-dioxane; hydrocarbons and halogenated hydrocarbons such as hexane, heptane, cyclohexane, methylcyclohexane, toluene, ortho-xylene, meta-xylene, para-xylene, mesitylene, chlorobenzene or ortho-dichlorobenzene. Preference is given to using tetrahydrofuran (THF) or 2-methyl-THF.

Examples of useful organic bases for the process according to the invention include the following: triethylamine, diethyl-iso-propylamine, tri-n-butylamine, pyridine, picoline, lutidine and collidine. Preference is given to using triethylamine Useful organometallic reagents for the process according to the invention include: methyllithium, methylmagnesium iodide, methylmagnesium bromide and methylmagnesium chloride. Preference is given to the use of methylmagnesium bromide and methylmagnesium chloride.

The temperature in the process according to the invention can be varied within wide limits. A customary operating temperature is from −10° C. to 20° C. Preferably, the reaction is conducted at a temperature in the range from −5° C. to 20° C.

The process according to the invention is typically conducted at standard pressure. It is also possible to conduct the reaction under reduced pressure or under elevated pressure.

In step (ii) of the process according to the invention, the molar ratios of the compound of the formula (IV) to the organometallic reagent and to the organic base may vary within wide ranges. They are generally not subject to any restriction.

In step (ii), it is preferable when the molar ratio of the organometallic reagent to the compound of the formula (IV) is in the range from 1.0 to 3.0, more preferably in the range from 1.2 to 2.5. Most preferably, the molar ratio is in the range from 1.5 to 2.3. It is additionally preferable when the ratio of the organometallic reagent to the organic base is in the range from 0.8 to 1.5, more preferably in the range from 0.9 to 1.1.

The reaction time is short and is in the range from about 0.5 to about 5 hours. A longer reaction time is possible, but is not economically worthwhile.

The transformation of esters to ketones using a Grignard reagent with an organic base is known from the literature (see, for example, Baraldi, Pier Giovani et al *Tetrahedron* 1987, 43(1), 235-42).

Step (iii):

Reacting the compound of the formula (Ia) with a halogenating agent in a solvent to give the haloketone (Ib).

Useful halogenating agents for the process according to the invention include chlorine and bromine, preferably bromine.

Useful solvents for the process according to the invention include the following solvents or solvent mixtures: nitriles, for example acetonitrile and butyronitrile; ethers, for example dimethoxyethane (DME), tetrahydrofuran (THF), 2-methyl-THF and 1,4-dioxane; hydrocarbons and halogenated hydrocarbons such as hexane, heptane, cyclohexane, methylcyclohexane, toluene, ortho-xylene, meta-xylene, para-xylene, mesitylene, dichloromethane, chlorobenzene, ortho-dichlorobenzene or nitrobenzene; esters, for example methyl acetate, ethyl acetate, n-propyl acetate, isopropyl acetate, n-butyl acetate, isobutyl acetate, sec-butyl acetate, hexyl acetate, cyclohexyl acetate, 2-ethylhexyl acetate, organic acids (for example acetic acid). Preferably, dichloromethane, acetic acid or dioxane is used, more preferably dioxane or acetic acid.

The temperature in the process according to the invention can be varied within wide limits. A customary operating temperature is from 0° C. to 120° C., preferably from 20° C. to 100° C., more preferably from 20° C. to 40° C.

The process according to the invention is typically conducted at standard pressure. It is also possible to conduct the reaction under reduced pressure or under elevated pressure.

In step (iii) of the process according to the invention, the molar ratios of the compound of the formula (Ia) to the halogenating agent may vary within wide ranges. They are generally not subject to any restriction.

In step (iii), it is preferable when the molar ratio of compound of the formula (Ia) to the halogenating agent is in the range from 1.5 to 0.9, more preferably in the range from 1.3 to 1.1. Most preferably, the molar ratio is in the range from 1.1 to 1.0.

The reaction time is short and is in the range from about 0.5 to about 5 hours. A longer reaction time is possible, but is not economically worthwhile.

EXAMPLES

The present invention is elucidated in detail by the examples which follow, without restricting the invention to these examples.

Example 1

Ethyl 5-{2-chloro-6-[(methylsulphonyl)oxy]phenyl}-4,5-dihydro-1,2-oxazole-3-carboxylate

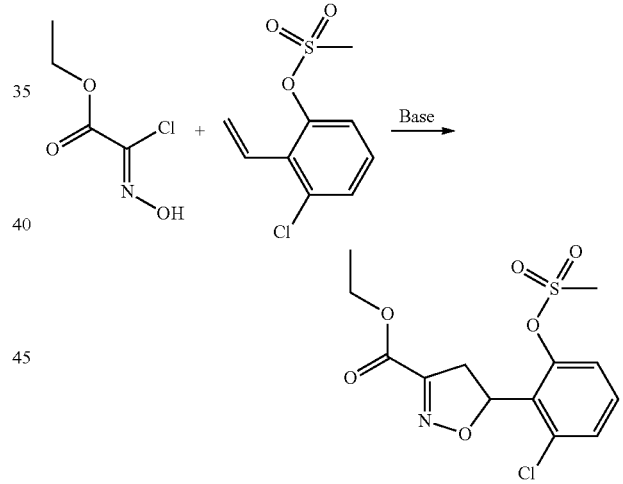

To a mixture of 57.0 g (237 mmol) of 3-chloro-2-vinylphenyl methanesulphonate (content: 96.7%) in 50 ml of ethyl acetate are added 54.4 g (355 mmol) of ethyl 2-chloro (hydroxyimino)acetate in 200 ml of ethyl acetate and 125 g (1.48 mol) of sodium hydrogencarbonate. The mixture is left to stir at 20-25° C. for 1.5 hours and then heated to 40° C. for a further 2 hours. After cooling to room temperature, 500 ml of water are added and the lower, aqueous phase is removed. To the organic phase are added 100 ml of a 1 N aqueous hydrochloric acid and 100 ml of a saturated sodium chloride solution. The organic phase is freed of the solvent on a rotary evaporator, and the residue is crystallized from hexane and tert-butyl methyl ether. This affords 70.6 g of ethyl 5-{2-chloro-6-[(methylsulphonyl)oxy]phenyl}-4,5-dihydro-1,2-oxazole-3-carboxylate having a content of 99.2% in the form of a colourless solid (yield: 85%).

$^1$H NMR (CD$_3$CN): 1.37 (t, 3 H), 3.35 (s, 3 H), 3.38 (dd, 1 H), 3.59 (dd, 1 H), 4.31 (q, 2 H), 6.31 (dd, 1 H), 7.45-7.49 (m, 3 H) ppm.

Example 2

2-(3-Acetyl-4,5-dihydro-1,2-oxazol-5-yl)-3-chlorophenyl methanesulphonate

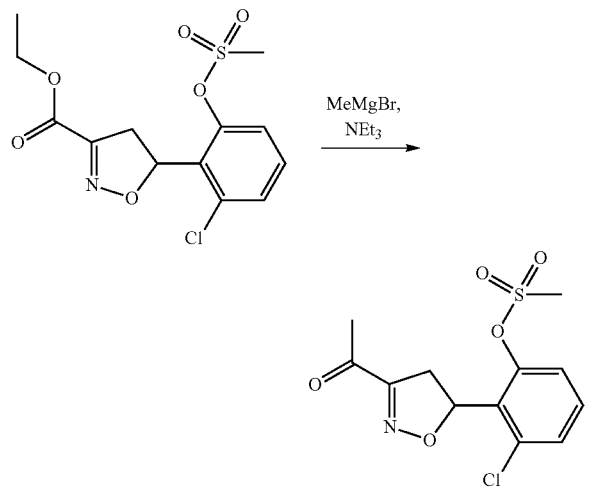

A solution of 100 g (279 mmol) of ethyl 5-{2-chloro-6-[(methylsulphonyl)oxy]phenyl}-4,5-dihydro-1,2-oxazole-3-carboxylate (content: 97.0%) in 500 ml of methyl-THF is cooled to −5° C. and 62.1 g (614 mmol) of triethylamine are added. Subsequently, 200 ml (641 mmol) of methylmagnesium bromide (3.2 molar solution in methyl-THF) are added at this temperature within 2 hours. The mixture is gradually added to 600 ml of hydrochloric acid in ice-water. The mixture is extracted first with 500 ml of ethyl acetate and then with 200 ml of ethyl acetate. The combined organic phases are freed of the solvent on a rotary evaporator and the residue is crystallized with 500 ml of heptane. This affords 87.8 g of 2-(3-acetyl-4,5-dihydro-1,2-oxazol-5-yl)-3-chlorophenyl methanesulphonate having a content of 91.5% in the form of a colourless solid (yield: 91%).

$^1$H NMR [(D6)-DMSO]: 2.47 (s, 3 H), 3.20 (dd, 1 H), 3.52 (dd, 1 H), 3.53 (s, 3 H), 6.26 (dd, 1 H), 7.50-7.58 (m, 3 H) ppm.

Example 3

2-[3-(Bromoacetyl)-4,5-dihydro-1,2-oxazol-5-yl]-3-chlorophenyl methanesulphonate

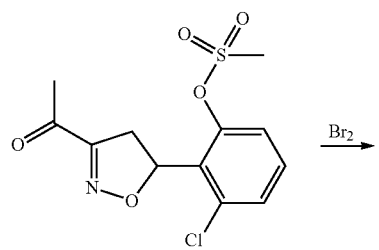

To a solution of 5.00 g (15.3 mmol) of 2-(3-acetyl-4,5-dihydro-1,2-oxazol-5-yl)-3-chlorophenyl methanesulphonate (content: 97.3%) in 20 ml of dioxane are added dropwise, at 20-25° C., 2.2 g (13.8 mmol) of bromine. After 2 hours, 10 ml of water and 2×20 ml of dichloromethane are added. The combined organic phases are washed with 20 ml of sodium sulphite solution and the organic phase is freed of the solvent on a rotary evaporator. This affords 6.34 g of 2-[3-(bromoacetyl)-4,5-dihydro-1,2-oxazol-5-yl]-3-chlorophenyl methanesulphonate having a content of 80.6% in the form of an orange oil (yield: 84%). The product is usable for the subsequent reactions without further purification.

$^1$H NMR (CD3CN): 3.33 (dd, 1 H), 3.35 (s, 3 H), 3.59 (dd, 1 H), 4.60 (s, 2 H), 6.33 (dd, 1 H), 7.44-7.47 (m, 3 H) ppm.

The invention claimed is:

1. Process for preparing one or more phenylisoxazoline derivatives of formula (I)

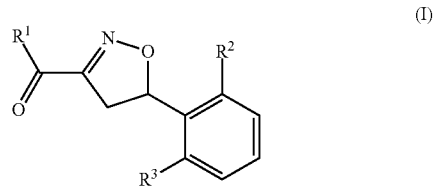

wherein

R$^1$ is methyl, bromomethyl or chloromethyl;

R$^2$ is halogen, C$_1$-C$_4$-alkyl, C$_1$-C$_4$-alkoxy, C$_1$-C$_4$-haloalkyl and R$^3$ is C$_1$-C$_4$-alkylsulphonyloxy, C$_1$-C$_4$-haloalkylsulphonyloxy, wherein, in (i), a chloroxime of formula (II)

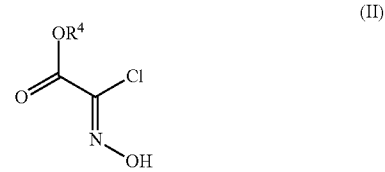

wherein R$^4$ is C$_1$-C$_{12}$-alkyl, is reacted with a styrene of formula (III)

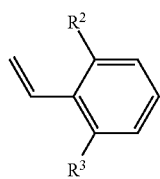

(III)

wherein R² and R³ are as defined above,
in the presence of an inorganic base in an organic aprotic solvent to give the corresponding phenylisoxazoline of formula (IV)

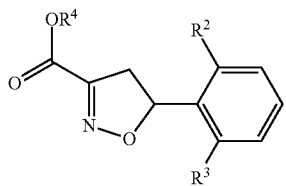

(IV)

wherein R², R³ and R⁴ are as defined above,
and the latter then reacts, in (ii), with an organometallic reagent and an organic base in an organic aprotic solvent to give the ketone of formula (Ia)

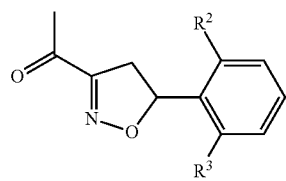

(Ia)

wherein R² and R³ are as defined above,
and then, in (iii), in the presence of a halogenating agent in a solvent, the haloketone of formula (Ib) is formed

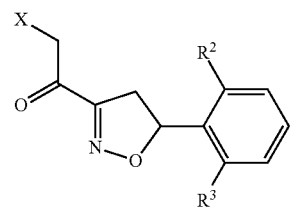

(Ib)

wherein R² and R³ are as defined above and
X is chlorine or bromine.

2. Process according to claim 1, wherein
$R^1$ is methyl, bromomethyl, chloromethyl;
$R^2$ is chlorine or bromine;
$R^3$ is methylsulphonyloxy or ethylsulphonyloxy;
$R^4$ is $C_1$-$C_4$-alkyl and
X is chlorine or bromine.

3. Process according to claim 1, wherein
$R^1$ is methyl, bromomethyl;
$R^2$ is chlorine;
$R^3$ is methylsulphonyloxy;
$R^4$ is methyl, ethyl and
X is bromine.

4. Process according to claim 1, wherein, in (ii), triethylamine is used as base and methylmagnesium bromide or methylmagnesium chloride as organometallic reagent.

* * * * *